(12) United States Patent
Mische

(10) Patent No.: US 6,375,666 B1
(45) Date of Patent: Apr. 23, 2002

(54) METHODS AND DEVICES FOR TREATMENT OF NEUROLOGICAL DISORDERS

(76) Inventor: Hans Alois Mische, 2221 Chelmsford La., St. Cloud, MN (US) 56301

( * ) Notice: Subject to any disclaimer, the term of this patent is extended or adjusted under 35 U.S.C. 154(b) by 0 days.

(21) Appl. No.: 09/457,971

(22) Filed: Dec. 9, 1999

(51) Int. Cl.⁷ .............................................. A61M 29/00
(52) U.S. Cl. ................................................... 606/198
(58) Field of Search ............................... 606/191–198; 623/1.15, 1.16, 1.22

(56) References Cited

U.S. PATENT DOCUMENTS 4,312,353 A * 1/1982 Shahbabian .................. 606/192
6,126,672 A * 10/2000 Berryman et al. ........... 606/198

* cited by examiner

*Primary Examiner*—Kevin Troung
(74) *Attorney, Agent, or Firm*—Crompton, Seager & Tufte, LLC

(57) ABSTRACT

A device controls various neurological disorders resulting from improper electrical conduction.

7 Claims, 6 Drawing Sheets

METHODS AND DEVICES FOR TREATMENT OF NEUROLOGICAL DISORDERS

FIELD OF INVENTION

The present invention relates generally to the treatment of electrical conduction defects in the body. The device and methods are disclosed in the context of treating neurologic disorders.

BACKGROUND OF THE INVENTION

The current methods of treating a range of neurological disorders include the use of systemic drugs, surgical procedures, tissue ablation, and gene treatments. Many of these disorders are manifested by gross conduction defects.

SUMMARY

In contrast to the prior art, the present invention proposes treatment of neurological disorder by subjecting selected tissues to localized mechanical stress. It is difficult to quantify the level of stress applied to the tissue; operable values will vary from low levels to high levels dependent on the type and location of tissue to be treated.

The invention is disclosed in the context of neurologic disorders but other organs and anatomical tissues are contemplated as well.

For example, other applications of this invention include placement in the pituitary, thyroid, and adrenal glands or in a variety of organs. In addition, placement of the inventive device in tumors may suppress growth due to nerve and vascular compression. The later may prevent blood-born metastasis to other parts of the body.

Likewise, hemorrhaging can be stopped or reduced by vascular compression using the invention. Pain management in all parts of the body can be achieved by placement of the inventive device adjacent to selected nerves. Positioning an inventive stress-inducing device within the bone can accelerate healing of broken bones. Disclosure of this invention for neurologic applications is intended to be illustrative and not limiting.

Many neurological disorders are a result of improper conduction of electrical currents in various brain tissues. In the case of Parkinson's disease, the conduction currents in the thalamus tissues become disorganized and cause conditions associated with the disease. Likewise, in epilepsy errant currents cause various levels of seizures. In cases of dystonia, errant currents originate in the basal ganglia. Depression and schizophrenia are associated with various conduction defects in other portions of the brain. Also, pain symptoms such as trigeminal neuralgia are associated with multiple sclerosis. Paralysis is normally a condition that results from brain injury, nerve damage, or nerve severing.

The localized stresses generated by the Mechanical Stress Device (MSD) will control, inhibit and direct current conduction by reorienting and/or reorganizing the electrical bias of the neurological tissues. In addition, applications for the MSD include compression of selected nerves in order to control, mediate, or suppress conduction along the nerve fibers and bundles that are associated with certain neurologic disorders.

The MSD can also be utilized as an electrically conductive device that creates an electrical connection or "bridge" between targeted anatomical tissues. This technique may facilitate tissue-to-tissue communication or aid in regenerating nerve connections.

In the case of Parkinson's disease, an MSD is implanted in the tissues proximate to the thalamus and induce localized stresses that cause depolarization of the thalamus tissue and thus eliminate or reduce the symptoms of the disease. In Dystonia, the MSD is positioned proximately to the basal ganglia and disrupts the electrical disturbances associated with this disorder.

The same effect is utilized in the treatment of epilepsy and other tissues when the MSD is installed in the target tissues. The devices and methods associated with the MSD can also be utilized in the sinuses and various ventricles of the brain to treat personality disorders such as schizophrenia or depression. Additionally, migraine headaches may be treated with the MSD technology. In general, the methods of the invention guide the placement of the device to ensure a therapeutic effect from the device.

The MSD can be permanently implanted or used acutely and then removed. Likewise, the device can be fabricated of biodegradable materials that are placed chronically and allowed to biodegrade over time.

The devices and methods can be used alone of in conjunction with other therapies.

Examples of electrical therapy are given and they include pacing, depolarization and ablation.

BRIEF DESCRIPTION OF THE DRAWINGS

Throughout the several views of the drawings several illustrative embodiments of the invention are disclosed. It should be understood that various modifications of the embodiments might be made without departing from the scope of the invention. Throughout the views identical reference numerals depict equivalent structure wherein.

DETAILED DESCRIPTION

The device and methods, which are similar to those discussed in the patent application filed on Nov. 19, 1999 by Mische entitled, "Mechanical Devices for the Treatment of Arrhythmias which is incorporated by reference herein.

Throughout the description the term mechanical stress device MSD refers to a device that alters the electrical conduction of physiologic tissues. The device may be made of metal such as Nitinol or Elgiloy and it may form an electrode for electrical stimulation. One or more electrodes may be associated with it. The MSD may incorporate fiber optics for therapeutic and diagnostic purposes. The device may also be made from a plastic or other non-metallic material. The MSD may also incorporate a covering of polymer or other materials. The MSD may also be a composition of different materials. The MSD may be smooth or have cutting or abrasive surfaces.

The MSD may be implanted for chronic use or for acute use. Biodegradable materials that degrade or dissolve over time may be used to form the MSD. Various coatings may be applied to the MSD including, but not limited to, thrombo-resistant materials, electrically conductive, non-conductive, thermo-luminescent, heparin, radioactive, or biocompatible coatings. Drugs, chemicals, and biologics such as morphine, dopamine, aspirin, lithium, Prozac, genetic materials, and growth factors can be applied to the MSD in order to facilitate treatment.

Other types of additives can be applied as required for specific treatments. Electrically conductive MSDs or MSDs with electrode elements may be used with companion pulse generators to deliver stimulation energy to the tissues. This electrical therapy may be used alone or in combination with other therapies to treat the various disorders. Electrical therapies may be supplied from implantable devices or they may be coupled directly to external generators. Coupling between the MSD and external generators can be achieved using technologies such as inductive or microwave coupling as examples. The MSD may also be designed of geometries or materials that absorb radioactive energies.

Figure 1:
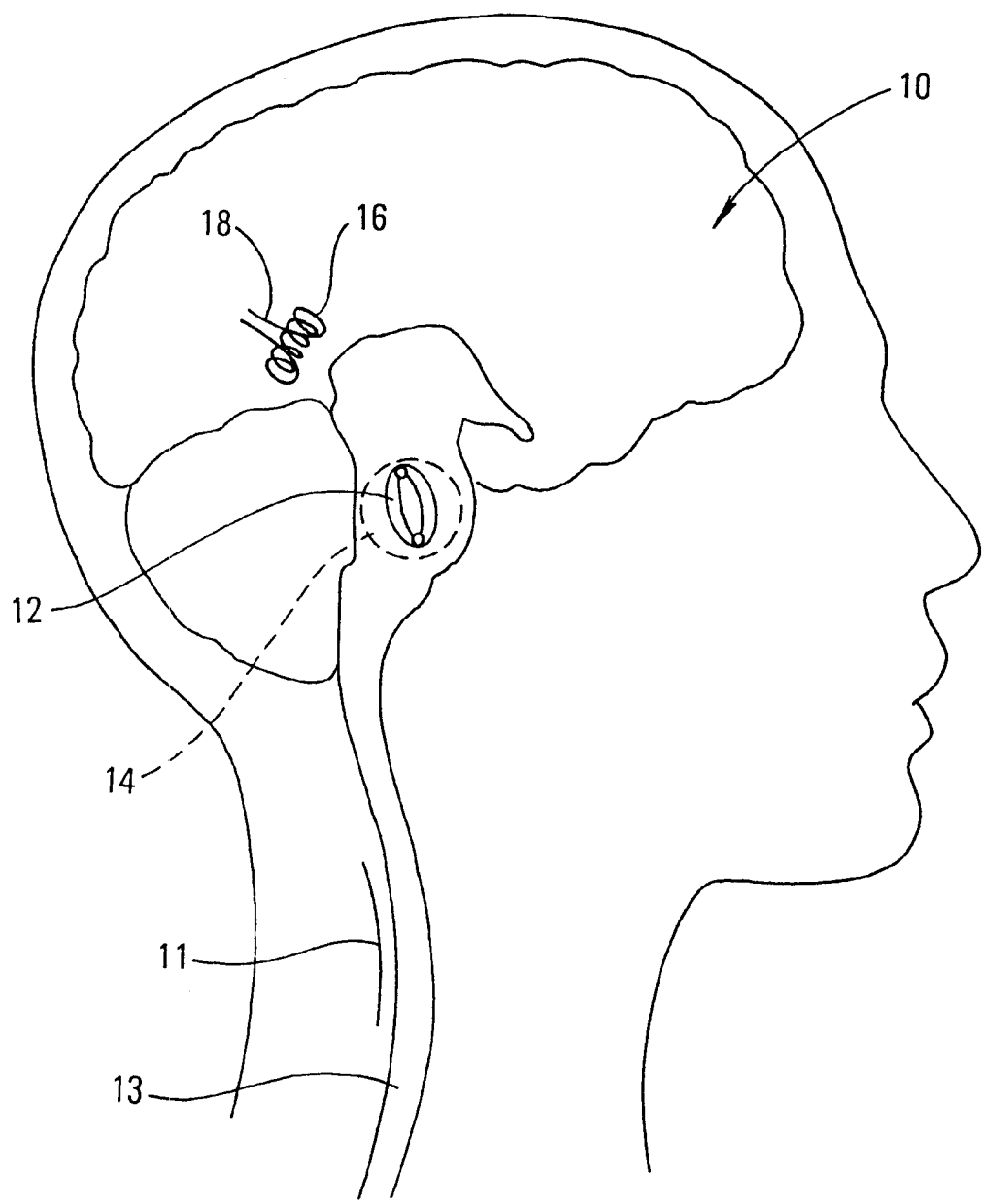
FIG. 1. is a schematic diagram of the head showing mechanical stress devices implanted within brain tissue.

FIG. 1 is a schematic diagram showing several possible locations and geometries for the mechanical stress device (MSD) within the brain 10. A multi-element splined MSD 12 is positioned proximate to the thalamus 14. In this case, the treatment is for Parkinson's Disease. A coil MSD 16 is positioned proximate to the trigeminal nerve 18 for treatment of trigeminal neuralgia. A wire form MSD 11 is positioned adjacent to the spinal cord 13.

Figure 2:
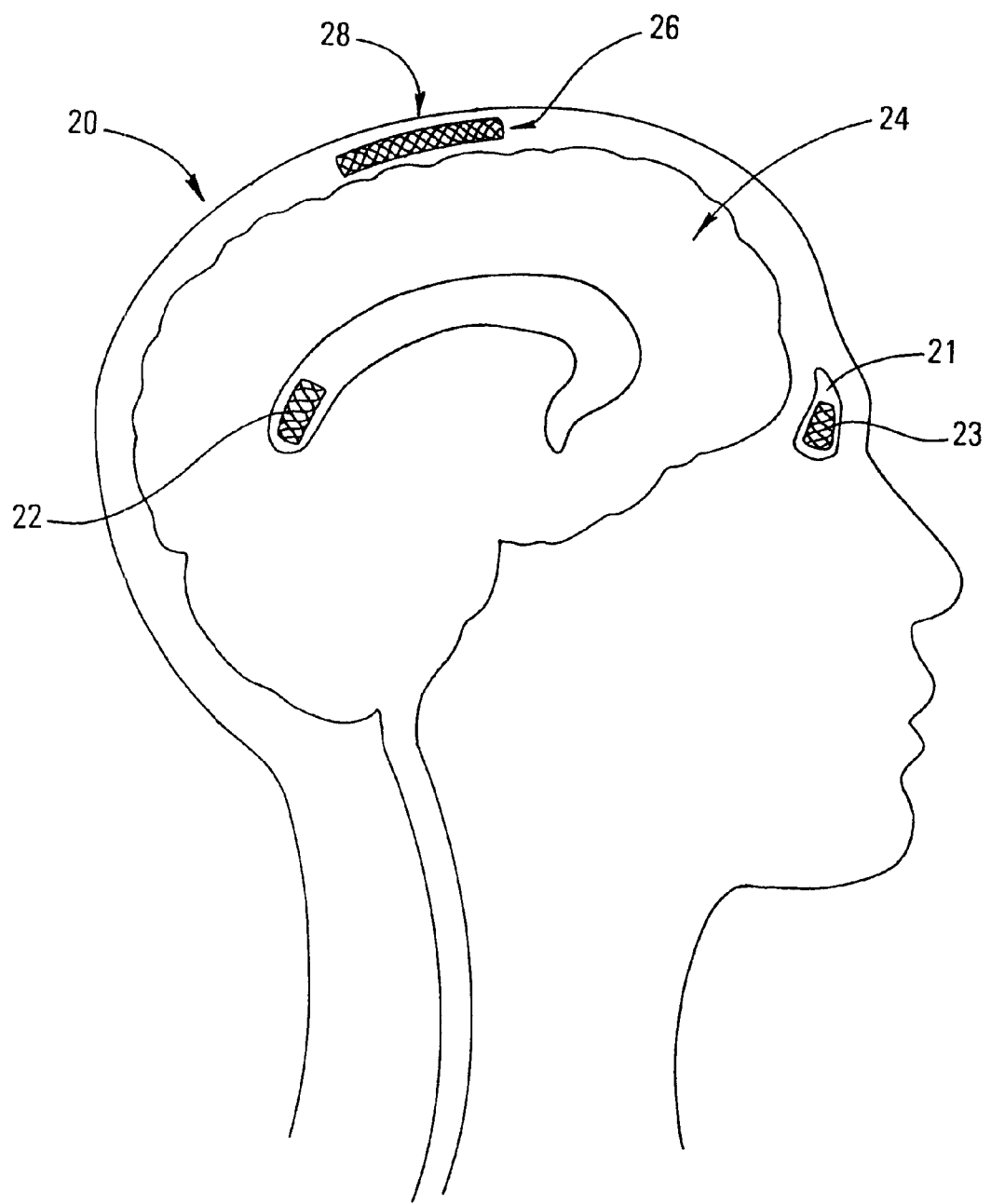
FIG. 2. is a schematic diagram of the head showing mechanical stress devices implanted in the frontal sinus, lateral ventricle of brain, and between the skull and brain tissue.

FIG. 2 is a schematic diagram of the head showing 20 various locations of MSDs of a tubular mesh form. An MSD 22 is located in the lateral ventricle of the brain 24. Another MSD 26 is positioned between the skull 28 and the brain 24.

Within the frontal sinus 21 an MSD 23 is positioned.

Figure 3:
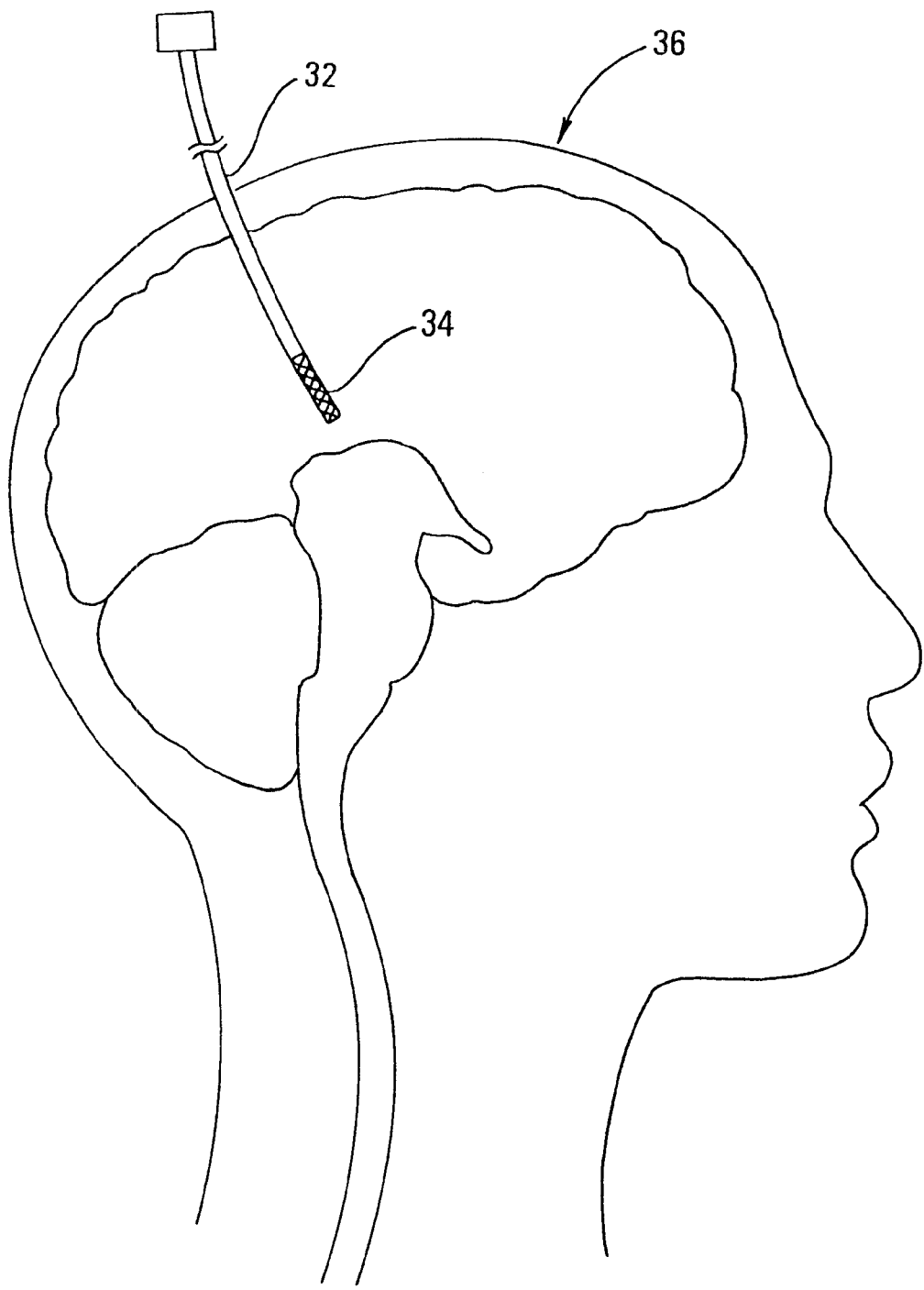
FIG. 3. is a schematic diagram of the head showing the mechanical stress device delivery system.
Figure 4:
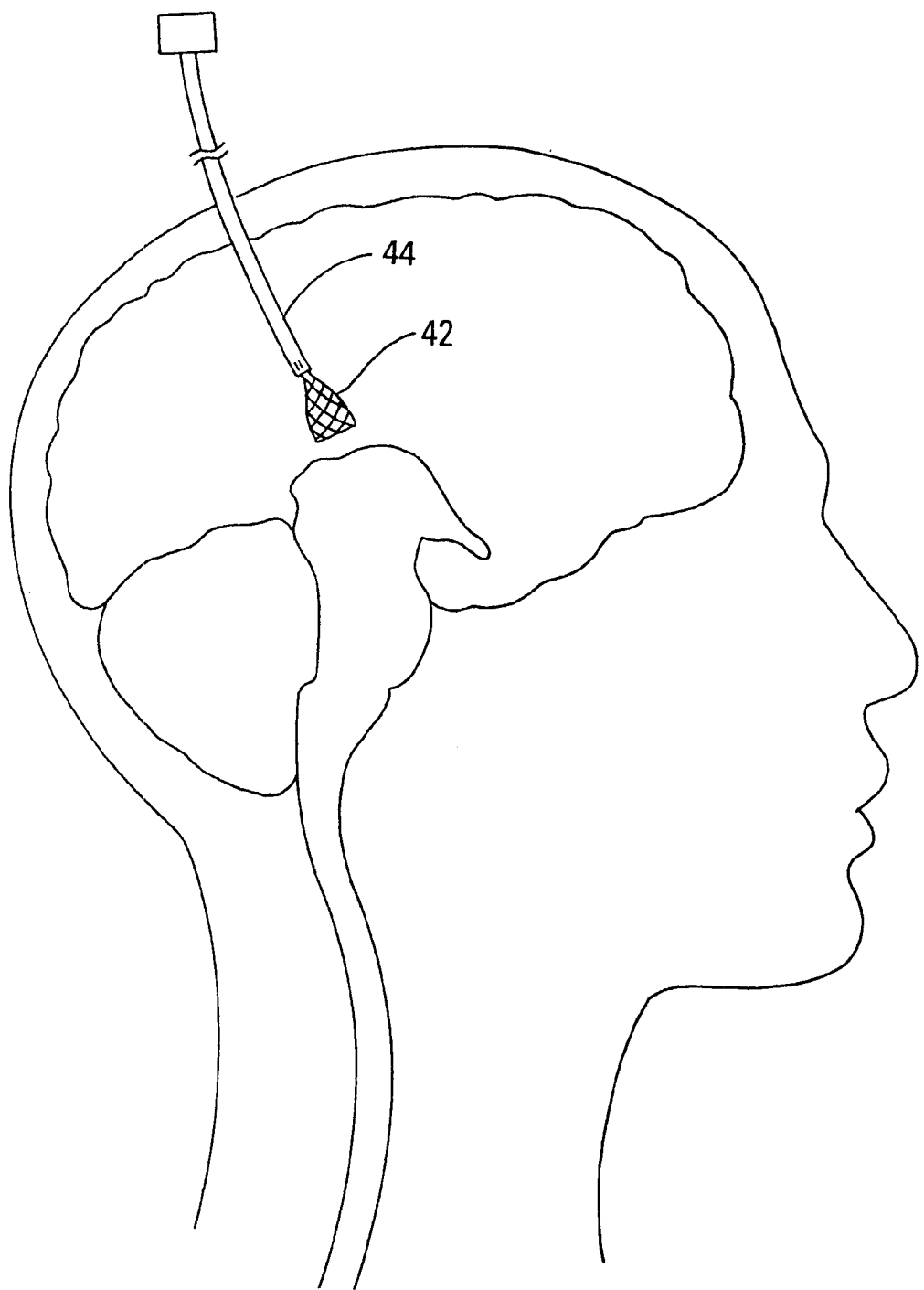
FIG. 4. is a schematic diagram of the head showing the mechanical stress device delivery system.

FIGS. 3 and 4 should be considered together. Together the two figure show the deployment of an MSD.

FIG. 3 is a schematic diagram of a tubular mesh type MSD delivery system. The tubular catheter 32 delivers the tubular mesh MSD 34. The first stage of implantation is navigation of the device to the selected site through the skull 36.

FIG. 4 shows the tubular mesh 42 expanding into position as it emerges from the lumen of the delivery catheter 44. In the self-expanding case, the tubular mesh has a predetermined maximum expandable diameter. The mesh can be made of a shape-memory material such as Nitinol so that when subjected to body temperature the structure expands. With shape memory materials, the shape of the expanded device can be predetermined. Additionally, the device can be retrieved, repositioned, or removed by using its shape memory characteristics. In general the MSD may be used acutely or chronically depending on the disease state of the patient.

Figure 5:
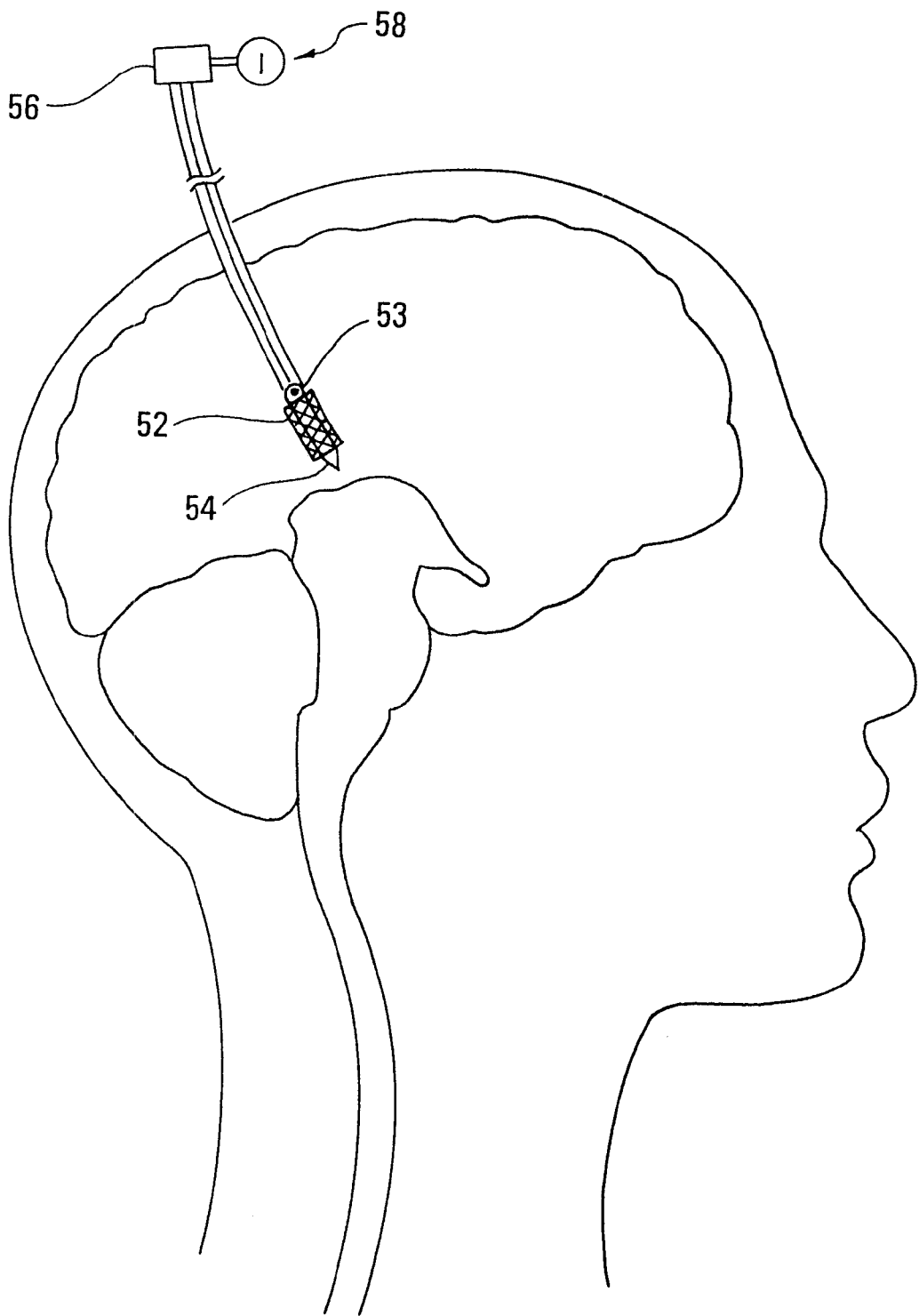
FIG. 5. is a schematic diagram of the head showing the mechanical stress device delivery system.

FIG. 5 shows an alternate balloon expanded MSD 52. In this alternate embodiment a balloon 54 may be used to expand the device within or proximate to selected tissues. In the balloon expandable case, the balloon may have a predetermined minimum or maximum diameter. In addition, the balloon shape can be made to provide proper placement and conformance of the device based on anatomical requirements and location. The balloon may be covered with electrically conductive material. The balloon may be inflated via a syringe 56 and a pressure gauge 58. For example an electrode site 53 may be connected to a remote pulse generator (not shown) to stimulate or ablate the site. The stimulator may activate the electrode either chronically or acutely.

Figure 6:
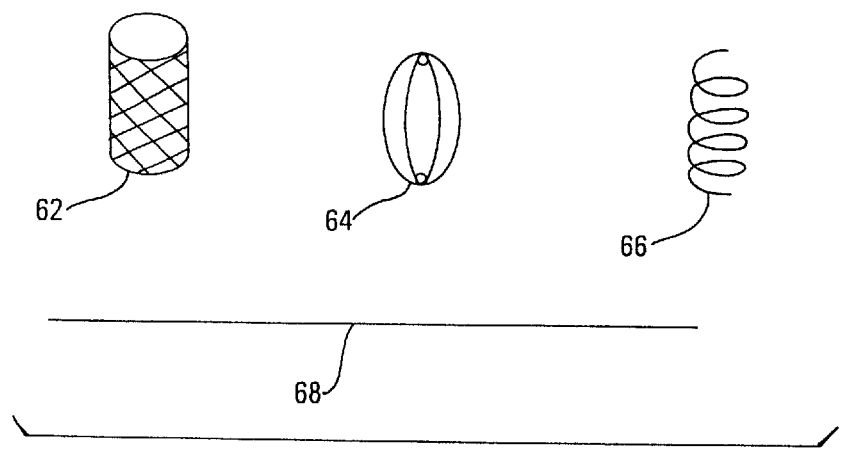
FIG. 6. shows a variety of MSD designs.

FIG. 6 shows a variety of possible MSD shapes and geometries. A tubular mesh 62, a multi-element spline 64, a coil 66, a wire 68 are all acceptable shapes for the MSD although each shape may be specifically adapted to a particular disease state.

Figure 7:
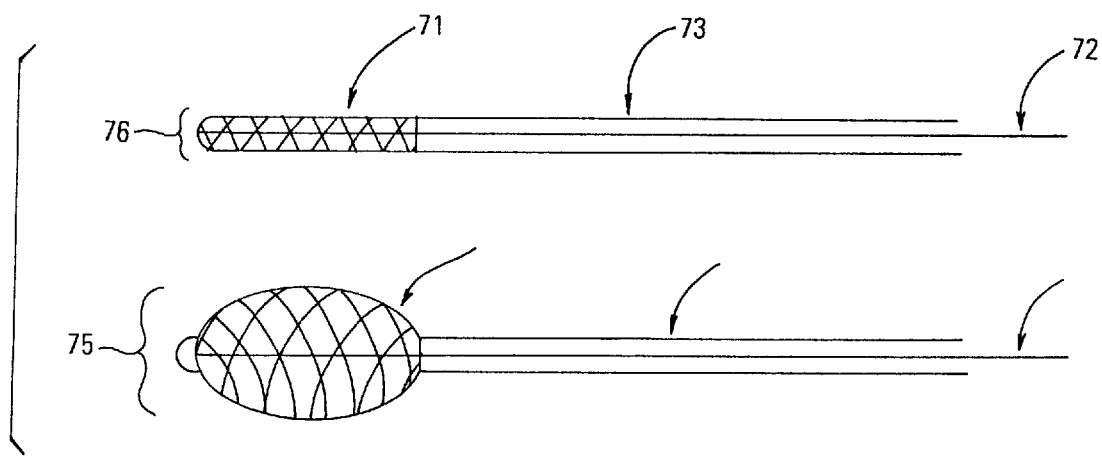
FIG. 7. depicts an MSD, which is manually expanded and contracted.

FIG. 7 shows two states of a manually expandable MSD device 71. The device consists of a coaxial shaft 72 and tube 73 arrangement. Attached to the distal end of the shaft 72 and the tube 73 is a braided mesh tube MSD 71. When the shaft 72 and tube 73 are moved opposite of the other by manipulating the proximal ends, the MSD 71 expands 75 or contracts 76. In this case, the MSD 71 can be made of any structure that expands and contracts such as a coil, splined-elements, etc. The various methods of expanding and contracting these structures are, but not limited to, push-pull, rotation, and balloon manipulation. In this type of device, direct connection to either an electrical generator, laser, or monitoring system can be made. In addition, it be envisioned that a device of similar nature be connected to a mechanical energy source, such as rotational or vibrational, in order to increase localized stresses.

The MSD can also utilize devices such as a balloon catheter, expanding devices, or wedges that impart stress or certain levels of localized trauma to selected tissues. The resultant stress and trauma affect the tissues so that current conduction in modified. It is envisioned that any of these devices can be used alone or in conjunction with other treatment modalities in order to provide the desired therapeutic result.

In general, the MSD will have a relaxed or minimum energy state. However the device or the implantation procedure should stretch or stress the device so that it applies a persistent force to the tissues to alter conduction in the strained tissues. In this sense the implanted MSD is not in a fully relaxed state after implantation. In some instances the MSD will cause the tissues to yield or tear generating altered conduction.

Preferably, the MSD is delivered in a minimally invasive procedure such via a catheter or other device. X-ray imaging, fluoroscopy, MRI, CAT scan or other visualization means can be incorporated into the procedural method. In general the devices may be introduced with cannulas, catheters or over guidewires through naturally occurring body lumens or surgically prepared entry sites. It should be apparent that other surgical and non-surgical techniques can be used to place the devices in the target tissue.

It should be apparent that various modifications might be made to the devices and methods by one of ordinary skill in the art, without departing from the scope or spirit of the invention.

What is claimed is:

1. A method of treating a neurological disorder involving an electrical conduction defect, comprising the steps of:
   identifying target tissue having the electrical conduction defect responsible for the neurological disorder;
   placing a mechanical stress device in said target tissue with a placement device;
   removing said placement device, whereby said mechanical stress device remains in said tissue; and
   whereby said mechanical stress device applies stress to said tissue to affect electrical conduction of said tissue to treat said neurological disorder.

2. A method as in claim 1, wherein said mechanical stress device occupies space and fills a volume within said tissue;
   said mechanical stress device generating localized stresses in said tissue, whereby electrical conduction proximate the location of localized stresses is altered.

3. A method as in claim 1, wherein said mechanical stress device comprises a tubular mesh for occupying space proximate to said tissue;

whereby the electrical conduction of said tissue proximate said tubular mesh is modified by the localized stresses imparted to said tissue.

4. A method as in claim 1, wherein said mechanical stress device comprises a multi-element device for occupying space proximate to said tissue and for generating localized stress;

whereby the electrical conduction of said tissue is modified by the localized stresses imparted to said tissue.

5. A method as in claim 1, wherein said mechanical stress device comprises a coil for occupying space proximate to said tissue;

whereby the electrical conduction of said tissue is modified by the localized stresses imparted to said tissue by said coil.

6. A method as in claim 1, wherein said mechanical stress device comprises a wire for occupying space proximate to said tissue;

whereby the electrical conduction of said tissue is modified by the localized stresses imparted to said tissue by said wire.

7. A method as in claim 1, wherein said mechanical stress device comprises a device for occupying space proximate to nerves in said tissue, said device creating localized stresses, whereby nerve conduction is modified.

* * * * *